US008765938B2

(12) United States Patent
Hara et al.

(10) Patent No.: US 8,765,938 B2
(45) Date of Patent: Jul. 1, 2014

(54) PROCESS FOR PRODUCTION OF POLYSACCHARIDE AND/OR MONOSACCHARIDE BY HYDROLYSIS OF DIFFERENT POLYSACCHARIDE

(75) Inventors: Michikazu Hara, Yokohama (JP);
Shinichiro Yanagawa, Yokohama (JP);
Akira Matsuo, Yokohama (JP);
Hidesato Kondo, Yokohama (JP)

(73) Assignees: Tokyo Institute of Technology, Tokyo (JP); Nippon Oil Corporation, Tokyo (JP)

( * ) Notice: Subject to any disclaimer, the term of this patent is extended or adjusted under 35 U.S.C. 154(b) by 808 days.

(21) Appl. No.: 12/304,916

(22) PCT Filed: Jun. 22, 2007

(86) PCT No.: PCT/JP2007/062612
§ 371 (c)(1),
(2), (4) Date: Feb. 5, 2009

(87) PCT Pub. No.: WO2008/001696
PCT Pub. Date: Jan. 3, 2008

(65) Prior Publication Data
US 2009/0176979 A1    Jul. 9, 2009

(30) Foreign Application Priority Data

Jun. 26, 2006  (JP) .................................. 2006-175225
Mar. 8, 2007   (JP) .................................. 2007-058546

(51) Int. Cl.
*C07H 1/08*  (2006.01)

(52) U.S. Cl.
USPC ........................................ 536/128; 536/124

(58) Field of Classification Search
CPC ........................................................ C07H 1/08
USPC ................................................ 536/124, 128
See application file for complete search history.

(56) References Cited

U.S. PATENT DOCUMENTS

| 4,239,633 | A | * | 12/1980 | Gutierrez et al. | ............ | 508/305 |
| 4,316,747 | A | * | 2/1982 | Rugg et al. | ...................... | 127/37 |
| 6,476,179 | B1 | * | 11/2002 | Ito et al. | ........................ | 528/196 |
| 8,017,724 | B2 | * | 9/2011 | Yanagawa et al. | ............ | 528/481 |
| 2006/0276668 | A1 | | 12/2006 | Domen et al. | | |

FOREIGN PATENT DOCUMENTS

| EP | 1 994 984 | 11/2008 |
| JP | 59-25801 A | 2/1984 |
| JP | 2002-85100 A | 3/2002 |
| JP | 2004-238311 A | 8/2004 |
| WO | WO-2005/029508 A1 | 3/2005 |

OTHER PUBLICATIONS

Extended European Search Report in corresponding EP Application No. 07767421.6 dated Nov. 11, 2009.
Gelbard, G. "Organic Synthesis by Catalysis with Ion-Exchange Resins" Industrial and Engineering Chemistry Research, (2005) vol. 44, No. 23, pp. 8468-8498.
Fukuoka, fine chemistry, May 2005, vol. 34, No. 5, pp. 11-18, fine chemical.
Fukuoka et al., Dai 96 Kai CatSJ Meeting a Yokoshu, 2005, p. 393.
Dhepe et al., CSJ: The Chemical Society of Japan Dai 85 Shunki Nenkai-Koen Yokoshu I, 2005, p. 53, 4 B4-06,.
Dhepe et al., Catalysis Letters, Aug. 2005, vol. 102, No. 3-4, p. 163-169.
Abbadi et al., Starch, 1998, vol. 50, No. 1, p. 23-28.
Hara, Chemistry, May 2006, vol. 61, No. 5, pp. 30 to 33.
Ichikawa et al., CSJ: The Chemical Society of Japan Dai 86 Shunki Nenkai-Koen Yokoshu I, Mar. 2006, p. 131, 2 D1-38, CSJ:..
Suganuma et al., CSJ: The Chemical Society of Japan Dai 87 Shunki Nenkai-Koen Yokoshu I, Mar. 2007, p. 490, 3 M2-18,.
Fontana et al., Cassava Starch Maltodextrinization/Monomerization Through Themopressurized Aqueous Phosphoric Acid Hydrolysis, Applied Biochemistry and Biotechnology, 2001, pp. 469-478, vol. 91-93.
Arai, Grafted Chain as Spacer for an Insoluble Polymer Catalyst, Journal of Applied Polymer Science, 1989, pp. 69-973, vol. 38.
Japanese Office Action dated Nov. 27, 2012 for Japanese Application No. JP2008-522545, with the English translation.
Matsuzawa et al., Hydrolysis of Sucrose in the Presence of Partially Sulfonated Poly(vinly Alcohol),Journal of Polymer Science, 1986, pp. 533-536, vol. 24.
Taneda, Bunriguytsu, 2004, pp. 130-133, vol. 34, No. 3.
Taneda, Concentrated Sulfuric Acid Biomass Ethanol Process, Cellulose Commun., Jun. 1, 2006, pp. 49-52, vol. 13, No. 2, with English abstract and English figures.
Taneda, Kagakusouchi, 2005, pp. 37-41, vol. 47, No. 3.

* cited by examiner

*Primary Examiner* — Patrick Lewis
*Assistant Examiner* — Everett White
(74) *Attorney, Agent, or Firm* — Birch, Stewart, Kolasch & Birch, LLP

(57) ABSTRACT

The object is to produce a polysaccharide and/or a monosaccharide efficiently by hydrolyzing a different polysaccharide efficiently. The hydrolysis of a polysaccharide is an important means for producing a monosaccharide that can be used as a starting material for the production of ethanol, the solubilization of a water-insoluble polysaccharide, and the production of a useful water-soluble low-polymeric saccharide or the like. For achieving the object, a polysaccharide to be hydrolyzed is reacted with water in the presence of a carbonaceous material having sulfonic acid group therein to cause the hydrolysis of the polysaccharide to be hydrolyzed, thereby producing a other polysaccharide and/or a monosaccharide.

14 Claims, No Drawings

PROCESS FOR PRODUCTION OF POLYSACCHARIDE AND/OR MONOSACCHARIDE BY HYDROLYSIS OF DIFFERENT POLYSACCHARIDE

FIELD OF THE INVENTION

The present invention relates to a process for producing a polysaccharide and/or a monosaccharide by hydrolyzing a different polysaccharide. The monosaccharide produced by the hydrolysis according to the present invention is useful as a starting material for the production of ethanol. Further, the hydrolysis of a polysaccharide to produce a low-polymeric saccharide is advantageous from the industrial viewpoint. The process for converting a water-insoluble polysaccharide into a chemically useful water-soluble saccharide is also extremely important from the industrial viewpoint.

BACKGROUND ART

In recent years, the hydrolysis of a polysaccharide (e.g., cellulose or starch that comprises a plant body) to produce a monosaccharide that can be fermented with yeast or the like has been focused as an essential technique for producing a clean fuel "bioethanol". The hydrolysis of a polysaccharide is also important, not only for the production of a monosaccharide, but also as a method for producing a chemically or nutritionally useful substance. Not only the hydrolysis of a water-insoluble cellulose or the like into a water-soluble substance is important as a means for producing a chemically or nutritionally useful substance, but the hydrolysis also enables to produce a monosaccharide readily through enzymatic saccharification of the water soluble substance which produced by the hydrolysis of the water-insoluble cellulose or the like. The monosaccharide can be used for the production of "bioethanol" through fermentation or the like. Thus, the hydrolysis of a water-insoluble polysaccharide is highly valuable from the industrial viewpoint. In the hydrolysis reaction, up to this time, either of "a concentrated sulfuric acid method" or "a diluted sulfuric acid method" has been employed (Non-patent reference No. 1). In the "concentrated sulfuric acid method", a polysaccharide is hydrolyzed in concentrated sulfuric acid. However, an enormous amount of energy is required for separating a product of the reaction, such as a monosaccharide or a water-soluble hydrolysate, from sulfuric acid. In the "diluted sulfuric acid method" utilizing diluted sulfuric acid of 100° C. or higher, on the other hand, an enormous amount of energy is required not only for the separation of a product such as a monosaccharide or a water-soluble hydrolysate from sulfuric acid, but also for the reaction itself. When a solid acid which can be separated from a product readily is used as a catalyst, a large amount of energy cost can be saved. However, there is found no solid acid that can hydrolyze a polysaccharide such as cellulose or starch that comprises a plant body and enables to produce a monosaccharide capable of being fermented with yeast or the like or a chemically useful intermediate such as a low-polymeric saccharide efficiently. Study has been made on the method for decomposing cellulose with an enzyme. However, the method has such problems that an expensive enzyme must be used and that the hydrolytic activity of an enzyme used is low (Non-patent reference No. 2).

The present inventors found that a carbonaceous material having sulfonic acid group therein which is characterized by being produced by the carbonization and sulfonation of an organic material can act as a catalyst, and filed patent applications previously (Patent reference Nos. 1 and 2). However, the patent applications do not describe about a fact that the carbonaceous material can hydrolyze a polysaccharide.

[Non-patent reference No. 1] Bionics, 2006, vol. 2, p. 26-33
[Non-patent reference No. 2] Cellul Chem Technol vol. 26, p 3-10
[Patent reference No. 1] Japanese Patent Application Laid-open No. 2004-238311
[Patent reference No. 2] International Publication No. WO 2005/029508 pamphlet

DISCLOSURE OF THE INVENTION

Problems to be Solved by the Invention

As mentioned above, for hydrolyzing a polysaccharide such as cellulose or starch that comprises a plant body to produce a hydrolysate such as a monosaccharide capable of being fermented with yeast or a water-soluble low-polymeric saccharide, it is needed to use sulfuric acid or the like, and an enormous energy is required for separating sulfuric acid from a product. In these technical situations, the object of the present invention is to provide: a means for efficiently producing a monosaccharide, which can be used as a starting material for the production of ethanol, from a polysaccharide; an efficient means for producing a chemically useful low-polymeric saccharide through hydrolysis; an efficient means for converting a water-insoluble polysaccharide into a water-soluble low-polymeric saccharide; a hydrolysis reaction for a polysaccharide, which can eliminate many of the steps that are needed in the conventional processes utilizing a mineral acid catalyst, particularly a sulfuric acid catalyst, or simplify the steps, can prevent the corrosion of an apparatus, and can achieve the same level of reaction efficiency as that in the conventional processes, by using a carbonaceous material having sulfonic acid group therein; and a process for producing a monosaccharide through the hydrolysis reaction.

Means for Solving the Problems

In order to solve the problems as mentioned above, the present inventors have made intensive and extensive studies. As a result, it is found that a carbonaceous material having sulfonic acid group therein, which was developed by the present inventors previously and is characterized by being produced by the carbonization and sulfonation of an organic material, can hydrolyze a polysaccharide including a water-insoluble polysaccharide (e.g., cellulose) efficiently into a different polysaccharide and/or a monosaccharide. Based on the finding mentioned above, the present invention has been accomplished.

Heretofore, it has been believed that, for the purpose of hydrolyzing a polysaccharide such as cellulose with an acid, the acid must move to the binding site between saccharide units, and therefore only a liquid acid such as sulfuric acid can hydrolyze the polysaccharide. In fact, a solid acid "Nafion" cannot hydrolyze cellulose (see Comparative example 2 in Experiment-1). Therefore, it is wholly unexpected at the time of filing the present application that the above-mentioned carbonaceous material, which is a solid acid, can hydrolyze a polysaccharide.

Surprisingly, however, when the carbonaceous material having sulfonic acid group therein is used, the reaction proceeds with the same degree of efficiency as that in a reaction using a sulfuric acid catalyst, and the hydrolysis proceeds even when the substrate is a solid material such as cellulose.

These results, which are unexpected from the conventional knowledge, lead to the accomplishment of the present invention.

Thus, the present invention has been accomplished based on the above-mentioned findings.

That is, the present invention provides the following items (1) to (15).

(1) A process for producing a polysaccharide and/or a monosaccharide, which comprises hydrolyzing a different polysaccharide in the presence of a carbonaceous material having sulfonic acid group therein.

(2) The process for producing a polysaccharide and/or a monosaccharide according to item 1, wherein the carbonaceous material having sulfonic acid group therein is produced by carbonizing and sulfonating an organic material.

(3) The process for producing a polysaccharide and/or a monosaccharide according to items 1 or 2, wherein the carbonaceous material having sulfonic acid group therein has sulfonic acid density of 1 mmol/g or more, and shows a Raman spectrum in which the integral intensity ratio of D band to G band is 0.7 or less or shows no Raman spectrum.

(4) The process for producing a polysaccharide and/or a monosaccharide according to any one of items 1 to 3, wherein the polysaccharide to be produced is a water-soluble polysaccharide.

(5) The process for producing a polysaccharide and/or a monosaccharide according to any one of items 1 to 4, wherein the polysaccharide to be hydrolyzed is cellulose.

(6) The process for producing a polysaccharide and/or a monosaccharide according to any one of items 1 to 5, wherein the organic material is a woody plant and/or a herbaceous plant.

(7) The process for producing a polysaccharide and/or a monosaccharide according to any one of items 1 to 6, wherein carbonaceous material having sulfonic acid group therein is produced by carbonizing a woody plant and/or a herbaceous plant at a temperature of 300 to 600° C. and subsequently sulfonating the resulting products with concentrated sulfuric acid or fuming sulfuric acid at a temperature of 50 to 250° C.

(8) The process for producing a polysaccharide and/or a monosaccharide according to any one of items 1 to 5, wherein the organic material is cellulose.

(9) The process for producing a polysaccharide and/or a monosaccharide according to any one of items 1 to 5, wherein the organic material is a phenolic resin.

(10) The process for producing a polysaccharide and/or a monosaccharide according to any one of items 1 to 9, wherein the polysaccharide to be hydrolyzed is a material having a β1-4 glycosidic bond.

(11) The process for producing a polysaccharide and/or a monosaccharide according to item 10, wherein the material having a β1-4 glycosidic bond is cellulose.

(12) The process for producing a polysaccharide and/or a monosaccharide according to item 10, wherein the material having a β1-4 glycosidic bond is a material comprising cellobiose.

(13) The process for producing a polysaccharide and/or a monosaccharide according to item 10, wherein the material having a β1-4 glycosidic bond is lignocellulose.

(14) The process for producing a polysaccharide and/or a monosaccharide according to any one of items 1 to 11, wherein the monosaccharide is glucose.

(15) A method for solubilizing cellulose or hemicellulose in water, which comprises reacting water with cellulose or hemicellulose in the presence of a carbonaceous material having sulfonic acid group therein.

Effect of the Invention

As mentioned above, when the hydrolysis is carried out using a liquid acid catalyst, an enormous amount of energy is required for the separation of the acid. In the process according to the present invention, a solid carbonaceous material having sulfonic acid group therein is used as a catalyst. Therefore, there is no concern about the corrosion of an apparatus, the catalyst can be separated readily from a product compared with a process using a conventional sulfuric acid catalyst. Thus, in the process of the present invention, the steps for catalyst separation, recovering, purification, concentration, recycling, waste water processing and the like can be largely eliminated or simplified, and the same level of reaction efficiency as that in a conventional process can be achieved. Therefore, the process of the present invention enables to hydrolyze cellulose at low cost and with a high degree of efficiency.

BEST MODE FOR CARRYING OUT THE INVENTION

Hereinbelow, the present invention will be described in detail.

[Catalyst]

Firstly, description will be made on a carbonaceous material having sulfonic acid group therein, which is used in the hydrolysis of a polysaccharide according to the present invention and in the process for producing a polysaccharide and/or a monosaccharide through the hydrolysis.

The term "a carbonaceous material having sulfonic acid group therein" (also referred to as "a sulfonic acid-group-containing carbonaceous material") as used herein refers to a carbon having sulfonic acid group therein and having no definite crystalline structure like that of diamond or graphite.

The sulfonic acid-group-containing carbonaceous material to be used is not particularly limited, as long as it can hydrolyze a polysaccharide. For example, an amorphous carbon having sulfonic acid group therein as disclosed in International Publication No. WO 2005/029508 pamphlet or a solid acid as disclosed in Japanese Patent Application Laid-open No. 2004-238311 can be used.

An preferred example of the sulfonic acid-group-containing carbonaceous material is a carbon which has both G band and D band detected in a spectrum obtained by Raman spectroscopy, wherein the integral intensity ratio of the D band to the G band [I(D)/I(G)] is preferably 0.7 or less, more preferably 0.65 or less, still more preferably 0.6 or less. Depending on the type of the raw material employed for producing the sulfonic acid-group-containing carbonaceous material, the sulfonic acid-group-containing carbonaceous material may have no spectrum observed. However, such a type of a sulfonic acid-group-containing carbonaceous material can also be used preferably. For a sulfonic acid-group-containing carbonaceous material produced by using cellulose as the raw material, the value of the [I(D)/I(G)] ratio may be 0.1 to 0.7. The terms "D band", "G band" and the "integral intensity ratio of D band to G band" as used herein are defined as follows.

D band is derived from an A1g breathing mode vibration in a 6-membered carbon ring, and its peak top appears at 1350 to 1360 $cm^{-1}$.

G band is derived from an E2g mode vibration in a 6-membered carbon ring, and its peak top appears at 1580 cm$^{-1}$±5 cm$^{-1}$.

A Raman spectrum formed from the sum of these peaks is separated into two peaks by Gaussian or Gaussian-Lorentzian. The obtained integral intensity values for D band and G band are employed as the integral intensities for these bands.

It is preferred that the sulfonic acid-group-containing carbonaceous material have an acid content of 1.0 mmol/g or more, more preferably 1.6 mmol/g or more, still more preferably 3 mmol/g or more. If the acid group content is lower than the lower limit of the above-mentioned range, then the activity of the sulfonic acid-group-containing carbonaceous material on the hydrolysis would be insufficiently. The upper limit of the acid content is not particularly limited.

In the sulfonic acid-group-containing carbonaceous material, the atomic ratio of a sulfur atom to a carbon atom (also referred to as "the sulfur/carbon atomic ratio") (by mole) is a measure of the amount of a sulfonic acid group added to or introduced into the sulfonic acid-group-containing carbonaceous material. In the present invention, the sulfur/carbon atomic ratio (by mole) in the sulfonic acid-group-containing carbonaceous material is $1.5 \times 10^{-2}$ or more. If the sulfur/carbon atomic ratio is lower than the lower limit, the activity of the sulfonic acid-group-containing carbonaceous material on the hydrolysis would be insufficient.

In the sulfonic acid-group-containing carbonaceous material used in the present invention, any structure cannot be confirmed based on an X-ray diffraction pattern. Therefore, the sulfonic acid-group-containing carbonaceous material is substantially amorphous.

The sulfonic acid-group-containing carbonaceous material can be produced by the heat treatment of an organic compound in concentrated or fuming sulfuric acid, as disclosed in International Publication No. WO 2005/029508 pamphlet.

For the purpose of producing a sulfonic acid-group-containing carbonaceous material having a high sulfonic acid density, it is required that the heating of an organic compound in concentrated or fuming sulfuric acid be carried out in the stream of an inert gas such as nitrogen or argon or in dried air. More preferably, concentrated or fuming sulfuric acid containing an organic compound is heated while blowing an inert gas (e.g., nitrogen, argon) or dried air therein. The reaction of concentrated sulfuric acid with an aromatic compound produces an aromatic sulfonic acid and water. This reaction is an equilibrium reaction. Therefore, if the amount of water in the reaction system increases, then the reaction proceeds rapidly in a reverse direction, resulting in the remarkable decrease in the amount of sulfonic acid groups introduced into the carbonaceous material. An amorphous carbon having a high sulfonic acid density can be synthesized by carrying out the reaction in the stream of an inert gas or dried air, or by carrying out the reaction while blowing the afore-mentioned gas into the reaction system and then removing water from the reaction system aggressively.

In the heat treatment, the partial carbonization, cyclization, condensation or the like of the organic compound is made to proceed and, at the same time, the sulfonation is made to occur. Therefore, the temperature for the heat treatment is not particularly limited, as long as the temperature enables the reaction to proceed. From an industrial viewpoint, the temperature is 50 to 450° C., preferably 60 to 350° C., more preferably 80 to 200° C. If the treatment temperature is lower than 50° C., then the condensation or carbonization of the organic compound is achieved unsatisfactorily, the carbon cannot be formed satisfactorily, and a sufficient amount of a sulfonic acid group cannot be introduced. If the treatment temperature is higher than 350° C., then the thermal decomposition of a sulfonic acid group would occur occasionally. When a polycyclic aromatic hydrocarbon is used as a starting material, it is preferred that the carbonization and the sulfonation be carried out simultaneously in one step.

The time for the heat treatment may be selected properly depending on the type of the organic compound or the treatment temperature employed, and is generally 1 to 50 hours, preferably 5 to 20 hours.

The amount of concentrated or fuming sulfuric acid used is not particularly limited, and is generally 2.6 to 50.0 moles, preferably 6.0 to 36.0 moles, per mole of the organic compound.

As the organic compound, an aromatic hydrocarbon may be used. Other organic compound such as a natural substance (e.g., glucose, sugar (sucrose), cellulose) may be also used preferably. Alternatively, a synthetic polymeric compound (e.g., polyethylene, polyacrylamide) may also be used. A woody material (e.g., cellulose, hemicellulose, lignin, lignocellulose) is preferred, since the sulfonic acid-group-containing carbonaceous material produced has high thermal stability. The woody or herbaceous material (i.e., a material containing cellulose, hemicellulose, lignin, lignocellulose or the like) may be used without purification. This case is preferred from the viewpoint of workability and economic advantage, since the labor of separation/purification of a cellulose component can be eliminated. The aromatic hydrocarbon may be a polycyclic or monocyclic aromatic hydrocarbon. Specific examples include benzene, naphthalene, anthracene, perylene and coronene, and naphthalene or the like is preferably used. A phenolic resin may be also used preferably. A synthetic polymeric material such as a phenolic resin enables to produce a sulfonic acid-group-containing carbonaceous material having a high acid content, and is therefore preferred. The organic compound may be used singly, or two or more types of organic compounds may be used in combination. The organic compound is not necessarily in a purified form. For example, heavy oil, pitch, tar, asphalt or the like which contains an aromatic hydrocarbon may be used.

When a natural substance such as glucose and cellulose or a synthetic polymeric compound is used as a raw material, it is preferred that the raw material be heated in an inert gas stream to cause the partial carbonization of the raw material prior to the heating treatment in concentrated sulfuric acid or fuming sulfuric acid. In this case, the temperature for the heating treatment is generally 100 to 600° C., and the time for the treatment is generally 1 minute to 100 hours, preferably 2 to 30 hours. If the temperature for the carbonization is lower than the lower limit of the above-mentioned range, then such a problem would occur that the heat resistance of the sulfonic acid-group-containing carbonaceous material produced by the sulfonation of the carbonized product is deteriorated or the amount of the sulfonic acid-group-containing carbonaceous material dissolved in water or an organic material is increased. If the temperature is higher than the upper limit of the above-mentioned range, then it would become impossible to introduce a sufficient amount of sulfonic acid groups during the sulfonation step, and the sulfonic acid-group-containing carbonaceous material produced would have an unsatisfactory level of a catalytic activity on the hydrolysis. If the time for the carbonization is shorter than the lower limit of the above-mentioned range, such a problem would occur that the heat resistance of the sulfonic acid-group-containing carbonaceous material produced by the sulfonation of the carbonized product is deteriorated or the amount of the sulfonic acid-group-containing carbonaceous material dissolved in water or an organic material is increased. A satisfactory degree of the carbonization can proceed within the time of the upper limit of the above-mentioned range. Therefore, the carbonization carried out for a time period longer than the upper limit is not necessary and is not desirable, since an excess amount of energy is consumed. When a woody or herbaceous plant or the like as mentioned above is used as a raw material to produce a sulfonic acid-group-containing carbonaceous material, it is also preferred that the raw material be heated in an inert gas stream to cause the carbonization of the raw material prior to the heating treatment in concentrated or fuming sulfuric acid. The temperature for the heating is preferably 300 to 600° C. The sulfonation after the carbonization can be carried out by using concentrated or fuming sulfuric acid under the above-mentioned conditions, and is preferably carried out at 50 to 250° C.

After the carbonization and sulfonation steps, a product is washed preferably with hot water to remove excess sulfuric acid from the product, and then dried, whereby the sulfonic acid-group-containing carbonaceous material according to the present invention can be produced. It is convenient to carry out the washing with hot water, for example, by a Soxhlet extraction method or the like under reflex at about 100° C. The washing may be carried out at a still higher temperature under pressure, thereby shortening the time period for the washing.

When an aromatic hydrocarbon or heavy oil, pitch, tar, asphalt or the like which contains an aromatic hydrocarbon is used as a raw material, it is preferred that, after the heating treatment in concentrated sulfuric acid or fuming sulfuric acid, a product produced by the heating treatment be heated in vacuo. This step enables to remove excess sulfuric acid, accelerate the carbonization or solidification of the product and increase the yield of the product. The vacuum evacuation is preferably conducted by using a vacuum evacuation apparatus having an outgassing rate of 10 L/min or more and an ultimate pressure of 100 torr or lower. The temperature for the heating is preferably 140 to 300° C., more preferably 200 to 280° C. The time for the vacuum evacuation at this temperature is generally 2 to 20 hours.

[Starting Material for Hydrolysis]

The sulfonic acid-group-containing carbonaceous material can hydrolyze a polysaccharide. Thus, as a process for producing a monosaccharide or a process for producing a hydrolysate such as a chemically useful different polysaccharide, provided is a process characterized by reacting a polysaccharide with water in the presence of a sulfonic acid-group-containing carbonaceous material to produce a hydrolysate such as a monosaccharide or a different polysaccharide.

The polysaccharide to be used is not particularly limited, as long as it can be hydrolyzed to produce a monosaccharide capable of being utilized in the ethanol fermentation and different polysaccharide such as water-soluble low-polymeric saccharide. Preferred examples of the polysaccharide to be used include naturally occurring water-insoluble polymeric materials such as a material comprising a molecule having a β1-4 glycosidic bond (e.g., cellulose, hemicellulose, lignocellulose). A water-soluble material comprising a molecule having a β1-4 glycosidic bond (e.g., cellobiose, cellobiose) may be also used. Starch (amylase, amylopectin), dextrin, maltose and the like are also exemplified. The polysaccharide may be in an unpurified form, so, a polysaccharide-containing natural organic raw material, such as a plant, may be also used. For example, a woody material (including a waste material), a waste paper, a rice straw, a wheat straw, a rice hull, a bamboo, a bagasse (a residue remaining after crushing a sugar cane), a corncob, a sago palm (a residue remaining after extracting starch from a crushed sago palm), a linter, a cotton, a pulp, or the like may be used as the raw material. These unpurified polysaccharides are same as the woody or herbaceous plants used as the starting materials for the production of a sulfonic acid-group-containing carbonaceous material to be used in the present invention. Therefore, the unreacted polysaccharide can be re-used for the reproduction of a sulfonic acid-group-containing carbonaceous material through the carbonization and sulfonation without the need of separating the unreacted polysaccharide from the sulfonic acid-group-containing carbonaceous material used. This fact is an advantage of the use of a woody plant and/or a herbaceous plant as the organic raw material for the production of the sulfonic acid-group-containing carbonaceous material according to the present invention.

The low-polymeric saccharide produced as the hydrolysate means a water-soluble polysaccharide or a polysaccharide actually dissolved in water. For example, with regard to a glucose polymer constituted via a β1-4 glycosidic bond, the low-polymeric saccharide refers to a polysaccharide having a glucose skeleton composed of about 2 to 10 repeating structures.

[Hydrolysis Reaction]

Though the amount of the sulfonic acid-group-containing carbonaceous material to be used relative to the amount of the starting material polysaccharide is not particularly limited, it is 0.1 to 100 g, preferably 1.0 to 30 g relative to 1 g of the starting material polysaccharide. If the ratio of the amount of the sulfonic acid-group-containing carbonaceous material as a catalyst to the amount of the starting material is smaller than $\frac{1}{10}$ or less, then the hydrolysis cannot proceed at a satisfactory rate. If the ratio of the amount of the sulfonic acid-group-containing carbonaceous material to the amount of the starting material is 100 times or more, then the facility cost is increased because of a large-capacity reactor or other facility, and the energy cost needed for heating, cooling and the like is also increased. So, it is not desirable.

The ratio of the amount of the starting material polysaccharide to the amount of water varies depending on the amount of the catalyst added, and therefore cannot be defined particularly. It is preferred to use water in an amount of 0.1 to 20 g, more preferably 0.5 to 10 g, relative to 1 g of the polysaccharide. If the ratio is 1:0.1 (starting material polysaccharide:water) or less, then a sufficient amount of water for the hydrolysis cannot be kept, and the efficient agitation in the reactor becomes difficult. If the ratio is 1:20 (starting material polysaccharide:water) or more, then the acid concentration in the reaction system is decreased, and the efficiency of the hydrolysis is decreased. However, this requirement is not particularly applied to a case where the sulfonic acid-group-containing carbonaceous material is supplied in a sufficient amount relative to the amount of the starting material. In this case, the amount of water can be increased to an amount at which a satisfactory level of reaction rate cannot be achieved substantially due to the decreased acid amount. However, even in this case, it is not preferred to supply water in an amount 10-times more than the amount of the sulfonic acid-group-containing carbonaceous material, from the viewpoint of reaction rate and the increase in energy cost required for heating, cooling and the like.

The reaction temperature for the hydrolysis according to the present invention is 20 to 250° C., preferably 60 to 150° C. A temperature lower than 20° C. is not preferred, since the hydrolysis cannot proceed at a satisfactory rate at this temperature. A temperature higher than 250° C. is not also preferred, since the sulfonic acid-group-containing carbonaceous material is deteriorated or the monosaccharide produced is further decomposed at this temperature.

The reaction pressure for the hydrolysis according to the present invention is not particularly limited. When the reaction is carried out at a temperature of 100° C. or higher, it is preferred to employ a pressure equal to or higher than the atmospheric pressure for the purpose of avoiding the vaporization of water.

When a vessel-type reactor equipped with a stirring apparatus is used, the reaction time for the hydrolysis according to the present invention is 20 minutes to 100 hours, preferably 20 minutes to 48 hours. If the reaction time is shorter than 20 minutes, then the hydrolysis cannot proceed sufficiently. If the reaction time is longer than 100 hours, then a large reaction vessel is needed and therefore the energy cost is increased. Further, the retention time becomes longer, and therefore the decomposition of the monosaccharide produced is accelerated and the yield of the monosaccharide is decreased.

The polysaccharide can be decomposed with the sulfonic acid-group-containing carbonaceous material into a monosaccharide or a water-soluble hydrolysate. In the hydrolysis reaction method according to the present invention, the hydrolysate may be collected after the polysaccharide is completely hydrolyzed, or may be separated and collected at any stage where the starting material polysaccharide still remains.

Hereinafter, the present invention will be described in great detail with reference to the following examples.

Experiment 1

Example 1

A cellulose powder (MERCK, K32941731) (20 g) was heated at 450° C. for 5 hours under a nitrogen gas stream to produce a carbonaceous powder. The powder was heated at 100° C. for 10 hours while stirring in 15-wt % fuming sulfuric acid (200 ml) to produce a black powder. The black powder was washed with distilled water repeatedly to remove sulfuric acid contained in the black powder, thereby producing a sulfonic acid-group-containing carbonaceous material.

The sulfonic acid-group-containing carbonaceous material had a sulfonic acid density of 1.2 mmol/g and an integral intensity ratio of D band to G band [I(D)/I(G)] in a Raman spectrum of 0.60.

The determination of a sulfonic acid density was made in the following manner. Since almost all of element sulfur contained in the sulfonic acid-group-containing carbonaceous material was derived from a sulfonic acid group, the amount of sulfur contained in a sample was quantified by elemental analysis by burning (SX-Elements Micro Analyzer YS-10 (yanaco)) to determine the amount of a sulfonic acid.

The integral intensity ratio of D band to G band in a Raman spectrum was determined in the following manner. A sample powder was placed in a sample holder in NRS-2100 type triple monochrometer Raman spectrometer (JASCO Corporation) and a Raman spectrum was measured. The Raman spectrum in which both D band and G band were observed was subjected to peak split into two peaks, i.e., D band and G band, using Gaussian or Gaussian-Lorentzian, and the obtained integral intensity values for D band and G band were employed as the integral intensities of these bands.

A mixture of a cellulose powder (MERCK, K32941731) (1 g) and water (5 g) was added with the sulfonic acid-group-containing carbonaceous material (1 g), and the resulting mixture was maintained at 80° C. to produce D-glucose. The amount of D-glucose produced was quantified by gas chromatography (Shimadzu IC-10A) The rate of production of D-glucose was 0.01 g/h.

Comparative Example 1

A sulfonic acid-group-containing carbonaceous material was produced in the same manner as in Example 1, except that the temperature for the heating cellulose was 650° C.

The sulfonic acid density and the integral intensity ratio of D band to G band [I(D)/I(G)] in a Raman spectrum of the sulfonic acid-group-containing carbonaceous material were determined in the same manner as in Example 1, and it was found that the sulfonic acid density and the integral intensity ratio of D band to G band [I(D)/I(G)] were 0.1 mmol/g and 0.73, respectively.

A mixture of a cellulose powder (MERCK, K32941731) (1 g) and water (5 g) was added with the sulfonic acid-group-containing carbonaceous material (1 g), and the resulting mixture was maintained at 80° C. to try to produce D-glucose. The amount of D-glucose produced was quantified, but D-glucose was not produced.

Comparative Example 2

The same experiment as in Example 1 was carried out, except that Nafion (a registered trade name), which is an already-existing solid catalyst having a high catalytic activity, was used in place of the sulfonic acid-group-containing carbonaceous material.

A mixture of a cellulose powder (MERCK, K32941731) (1 g) and water (5 g) was added with Nafion (NR50) powder (1 g), and the resulting mixture was maintained at 80° C. to try to produce D-glucose. The amount of D-glucose produced was quantified, but D-glucose was not produced.

Experiment 2

Examples and Comparative Examples

Catalyst Production Examples

[Production of Sulfonic Acid-Group-Containing Carbonaceous Materials]

As a catalyst raw material, powder of a composition [Dainippon Ink And Chemicals, Incorporated; Phenolite (a registered trade name) TD-739A] (a composition comprising 8 mass % of a curing agent hexamethylenetetramine in a novolak phenolic resin) (40 g) was charged in a 1000 ml-eggplant-shaped flask and heated at 400° C. for 5 hr under a nitrogen stream to produce a carbonized material (8.4 g). This black-colored powdery carbonized material (3 g) was added with concentrated sulfuric acid (150 g), and the mixture was heated at 150° C. for 2 hr in a nitrogen atmosphere to achieve the sulfonation. After the sulfonation, the black solid material was filtered through a glass filter, washed repeatedly with hot water under reflux (about 100° C.) by using a Soxhlet extractor, and it was confirmed that sulfuric acid was not detected in a washing water. The resulting product was dried to produce a black-colored powdery sulfonic acid-group-containing carbonaceous material A.

The same procedure as in the above-mentioned production process for the sulfonic acid-group-containing carbonaceous material A was carried out, except that 25% $SO_3$ fuming sulfuric acid (100 g) was used as the sulfonating agent to produce a sulfonic acid-group-containing carbonaceous material B.

The same procedures as in the above-mentioned production processes for the sulfonic acid-group-containing carbonaceous materials A and B were carried out, except that a cellulose powder (Aldrich; 310697) (40 g) was used as the catalyst raw material to produce sulfonic acid-group-containing carbonaceous materials C and D, respectively.

materials A and B, no clear spectrum could not be observed, and therefore it was difficult to calculate the degrees of graphitization. With regard to the sulfonic acid-group-containing carbonaceous materials C and D, on the other hand, a clear spectrum was observed, and the degrees of graphitization could be calculated.

TABLE 1

| | Production of sulfonic acid-group-containing carbonaceous materials | | | | | | Properties of sulfonic acid-group-containing carbonaceous materials | | | |
|---|---|---|---|---|---|---|---|---|---|---|
| Catalyst examples | Sulfonic acid-group-containing carbonaceous materials | Sterling materials | Conditions for carbonization | | Conditions for sulfonation | | Yield of carbonized materials (%) | Amount of acid groups (mmol/g) | Sulfur/carbon ratio (×10⁻²) | Graphitization degree |
| | | | Temperature (°C.) | Time (hr) | Sulfonating agent | Temperature (°C.) Time (hr) | | | | |
| 1 | A | Novolak phenolic resin | 400 | 4 | Conc. sulfuric acid | 150  2.0 | 21 | 2.79 | 3.7 | undetected |
| 2 | B | Novolak phonolic resin | 400 | 4 | Fuming sulfuric acid | 150  2.0 | 21 | 3.21 | 7.0 | undetected |
| 3 | C | Cellulose | 400 | 4 | Conc. sulfuric acid | 150  2.0 | 28 | 3.51 | 1.3 | 0.602 |
| 4 | D | Cellulose | 400 | 4 | Fuming sulfuric acid | 150  2.0 | 28 | 4.07 | 2.4 | 0.628 |
| Com. 1 | | Sulfuric acid | | | | | | — | — | — |
| Com. 2 | | Nafion | | | | | | 0.89⁽¹⁾ | — | — |
| Com. 3 | | Amberlyst | | | | | | 4.7⁽¹⁾ | — | — |

⁽¹⁾Values shown in catalogues

The sulfonic acid-group-containing carbonaceous materials thus produced were analyzed on the following items.

[Methods for Analysis of Sulfonic Acid-Group-Containing Carbonaceous Materials]

The sulfonic acid-group-containing carbonaceous materials were analyzed on the following items. The conditions for the production and the properties of each of the sulfonic acid-group-containing carbonaceous materials are shown in Table 1.

1. Powder X-Ray Diffractometry

For the analysis, an X-ray diffractometer (MXP18VAHF) manufactured by Mac Science Company Ltd. was used. In any one of the sulfonic acid-group-containing carbonaceous materials A to D, any peak specified from a diffraction pattern could not be detected, and it was found that the sulfonic acid-group-containing carbonaceous materials A to D were substantially amorphous.

2. Determination of Acid Group Content

The determination was carried out by a back-titration method.

3. Elemental Analysis

The analysis was made by using Elementar Vario EL. Each result is expressed by the ratio of a sulfur atom to a carbon atom (an S/C ratio). A value of the S/C ratio is a measure of the amount of a sulfonic acid group added to or introduced into a sulfonic acid-group-containing carbonaceous material.

4. Degree of Graphitization

For the purpose of determining a degree of graphitization, Raman spectroscopy was carried out. For the analysis, a laser Raman spectrometry HOLOLAB 5000R was used. Generally, the peak intensity ratio between D peak appearing at around 1400 cm⁻¹ and G peak appearing at around 1580 cm⁻¹ is employed as a measure of the degree of graphitization. With regard to the sulfonic acid-group-containing carbonaceous Reaction Examples Hydrolysis of Cellulose Distilled water (700 μl) and cellulose (MERCK; K32941731) (0.025 g) were charged in a 10 ml-eggplant-shaped flask, the sulfonic acid-group-containing carbonaceous material C (0.30 g) was added to the mixture, the flask was hermetically sealed and heated to 120° C. in an oil bath while stirring at 700 rpm, and the hydrolysis was carried out for 3 hr. After the reaction was completed, the reaction solution was cooled and centrifuged to cause the solid/liquid separation. The resulting product liquid was filtered through a microfilter. The amount of glucose in the solution obtained was quantified by liquid chromatography. The solution was evaporated to dryness to produce a residue. The amount of the residue was determined as a solubilized material content, and the solubilization ratio was calculated. The results are shown in Table 2.

The results obtained by varying the conditions such as temperatures, water contents and the types of the sulfonic acid-group-containing carbonaceous materials used are also shown in Table 2. As Comparative Examples, the results obtained by using sulfuric acid, Nafion and Amberlyst are also shown in Table 2.

[Hydrolysis of Cellobiose/Cellotriose/Cellohexose]

The hydrolysis was carried out under the same conditions and by the same procedures as mentioned above, except that each of cellobiose, cellotriose and cellohexose was used as a substrate in place of cellulose. The results are shown in Table 2.

[Hydrolysis of Lignocellulose]

The hydrolysis was carried out under the same conditions and by the same procedures as mentioned above, except that a eucalyptus powder (particle diameter: 0.2 mm) (as lignocellulose) was used as a substrate in place of cellulose. The results are shown in Table 2.

for 3 hr. After the reaction was completed, the reaction solution was cooled and centrifuged to cause the solid/liquid separation. The resulting liquid product was filtered through

TABLE 2

| Reaction examples | Catalyst Type | Catalyst Mass (g) | Substrate Type | Substrate Mass (g) | Water Mass (g) | Temperature °C. | Reaction time hr | Number rotations rpm | Hydrolysis Conversion of substrate (%) or amount of glucose produced (μmol) | Hydrolysis Ratio of solubilization (%) |
|---|---|---|---|---|---|---|---|---|---|---|
| 1 | C | 0.3 | Cellulose | 0.025 | 0.7 | 100 | 3 | 1000 | 3.5% | 71% |
| 2 | C | 0.3 | Cellulose | 0.025 | 0.7 | 120 | 3 | 500 | 12.30% | — |
| 3 | C | 0.3 | Lignocellulose | 0.025 | 0.7 | 100 | 3 | 1000 | 3.14 | 74% |
| 4 | C | 0.5 | Cellobiose | 0.5 | 3 | 100 | 24 | — | 63% | — |
| 5 | C | 0.3 | Cellotriose | 0.025 | 0.7 | 100 | 3 | — | 92% | — |
| 6 | C | 0.3 | Cellohexose | 0.025 | 0.7 | 100 | 3 | 1000 | 95% | — |
| 7 | A | 0.5 | Cellobiose | 0.5 | 3 | 100 | 24 | — | 86% | — |
| 8 | A | 0.5 | Cellobiose | 0.5 | 1 | 100 | 24 | — | 83% | — |
| 9 | B | 0.5 | Cellobiose | 0.5 | 1 | 100 | 24 | — | 90% | — |
| 10 | B | 0.3 | Cellulose | 0.025 | 0.7 | 100 | 3 | 1000 | 3.1% | — |
| Com. 1 | Sulfuric acid | 0.5 | Cellobiose | 0.09 | 1 | 100 | 24 | — | 95% | — |
| Com. 2 | Sulfuric acid | 0.3 | Cellotriose | 0.025 | 0.7 | 100 | 3 | 1000 | 49% | — |
| Com. 3 | Sulfuric acid | 0.3 | Cellulose | 0.025 | 0.7 | 100 | 3 | 1000 | 5.9% | 35% |
| Com. 4 | Sulfuric acid | 0.3 | Lignocellulose | 0.025 | 0.7 | 100 | 3 | 1000 | 5.8 | 28% |
| Com. 5 | Sulfuric acid | 0.3 | Cellohexose | 0.025 | 0.7 | 100 | 3 | 1000 | 41% | — |
| Com. 6 | Nafion | 0.3 | Cellulose | 0.025 | 0.7 | 100 | 3 | 1000 | undetected | — |
| Com. 7 | Amberlyst | 0.3 | Cellulose | 0.025 | 0.7 | 100 | 3 | 1000 | undetected | — |

Experiment 3

Example

Catalyst Production Example

[Production of Sulfonic Acid-Group-Containing Carbonaceous Material Using Woody Plant as Raw Material—1]

A eucalyptus powder (40 g) was charged in a 1000 ml-eggplant-shaped flask and heated at 400° C. for 4 hr under a nitrogen stream to produce a carbonized material (14 g). This black-colored powdery carbonized material (3.0 g) was added with concentrated sulfuric acid (150 g), and the mixture was heated at 150° C. for 2 hr in a nitrogen atmosphere to achieve the sulfonation. After the sulfonation, the black solid material was filtered through a glass filter, washed repeatedly with hot water under reflux (about 100° C.) by using a Soxhlet extractor, and it was confirmed that sulfuric acid was not detected in a washing water. The resulting product was dried to produce a black-colored powdery sulfonic acid-group-containing carbonaceous material E. The sulfonic acid-group-containing carbonaceous material thus produced was analyzed on the above-mentioned items. The powder X-ray diffractometry revealed that any peak specifying any structure could not be detected in the diffraction pattern, and it was found that the sulfonic acid-group-containing carbonaceous material E was substantially amorphous. The sulfonic acid-group-containing carbonaceous materials F and G produced in Experiments 4 and 5 were also substantially amorphous. Other results are shown in Table 3.

[Hydrolysis of Cellulose]

Distilled water (700 μl) and cellulose (MERCK; K32941731) (0.025 g) were charged in a 10 ml-eggplant-shaped flask, the sulfonic acid-group-containing carbonaceous material E (0.20 g) was added to the mixture, the flask was hermetically sealed and heated to 120° C. in an oil bath while stirring at 700 rpm, and the hydrolysis was carried out a microfilter. The amount of glucose in the solution obtained was quantified by liquid chromatography. The results are shown in Table 4.

Experiment 4

Example

Catalyst Production Example

[Production of Sulfonic Acid-Group-Containing Carbonaceous Material Using Woody Plant as the Raw Material—2]

A sulfonic acid-group-containing carbonaceous material F was produced under the same conditions as in Experiment 3, except that fuming sulfuric acid was used as a sulfonating agent. The sulfonic acid-group-containing carbonaceous material thus produced was analyzed on the above-mentioned items. The results are shown in Table 3.

[Hydrolysis of Cellulose]

The hydrolysis of cellulose was carried out under the same conditions as in Experiment 3, except that the sulfonic acid-group-containing carbonaceous material F was used as a catalyst, and the amount of glucose produced was determined. The results are shown in Table 4.

Experiment 5

Example

Catalyst Production Example

[Production of Sulfonic Acid-Group-Containing Carbonaceous Material Using Woody Plant as the Raw Material—3]

A sulfonic acid-group-containing carbonaceous material G was produced under the same conditions as in Experiment 3, except that an acacia powder was used as the raw material for the production of a sulfonic acid-group-containing carbonaceous material. The sulfonic acid-group-containing carbonaceous material thus produced was analyzed on the above-mentioned items. The results are shown in Table 3.
[Hydrolysis of Cellulose]
The hydrolysis of cellulose was carried out under the same conditions as in Experiment 3, except that the sulfonic acid-group-containing carbonaceous material G was used as a catalyst, and the amount of glucose produced was determined. The result is shown in Table 4.

TABLE 3

Sulfonic acid-group-containing carboneceous material production examples

| | Production of sulfonic acid-group-containing carbonaceous materials | | | | | | | Properties of sulfonic acid-group-containing carbonaceous materials | | |
|---|---|---|---|---|---|---|---|---|---|---|
| | Sulfonic acid-group- | | Conditions for carbonization | | Conditions for sulfonation | | | | | D/G peak intensity |
| | | | | | | | Yield of | Amount | Sulfur/ | |
| Experiment examples | containing carbonaceous materials | Raw materials | Temperature (° C.) | Time (hr) | Sulfonating agent | Temperature (° C.) | Time (hr) | Carbonized materials (%) | of acid groups (mmol/g) | carbon ratio (×10⁻²) | ratio in Raman spectrum |
| Experiment 3 | E | Eucalyptus | 400 | 4 | Conc. sulfuric acid | 150 | 2.0 | 36 | 2.98 | 1.7 | 0.572 |
| Experiment 4 | F | Eucalyptus | 400 | 4 | Fuming sulfuric acid | 150 | 2.0 | 36 | 3.95 | 2.8 | 0.576 |
| Experiment 5 | G | Acacia | 400 | 4 | Conc. sulfuric acid | 150 | 2.0 | 32 | 2.66 | 1.7 | 0.599 |

TABLE 4

Cellulose hydrolysis examples

| Experiment examples | Sulfonic acid-group-containing materials | Hydrolysis of cellulose Amount of glucose produced (μmol/g-cat/hr) |
|---|---|---|
| Experiment 3 | E | 4.9 |
| Experiment 4 | F | 1.2 |
| Experiment 5 | G | 1.0 |

The specification includes the contents as described in the specification and/or drawings of Japanese patent applications (Japanese Patent Application Nos. 2006-175225 and 2007-058546), which are priority documents of the present application. All publications, patents and patent applications cited herein are incorporated herein by reference in their entirety.

What is claimed is:

1. A process for producing a polysaccharide and/or a monosaccharide, which comprises hydrolyzing a different polysaccharide in the presence of a carbonaceous material having sulfonic acid group therein,
    wherein the carbonaceous material having sulfonic acid group therein is produced by carbonizing an organic material at a temperature of 300 to 600° C. and subsequently sulfonating the resulting products with concentrated or fuming sulfuric acid at a temperature of 50 to 250° C., and
    wherein the polysaccharide to be hydrolyzed is a water-insoluble polysaccharide.

2. The process for producing a polysaccharide and/or a monosaccharide according to claim 1, wherein the carbonaceous material having sulfonic acid group therein has sulfonic acid density of 1 mmol/g or more, and shows a Raman spectrum in which the integral intensity ratio of D band to G band is 0.7 or less or shows no Raman spectrum.

3. The process for producing a polysaccharide and/or a monosaccharide according to claim 1, wherein the polysaccharide to be produced is a water-soluble polysaccharide.

4. The process for producing a polysaccharide and/or a monosaccharide according to claim 1, wherein the polysaccharide to be hydrolyzed is cellulose.

5. The process for producing a polysaccharide and/or a monosaccharide according to claim 1, wherein the organic material is a woody plant and/or a herbaceous plant.

6. The process for producing a polysaccharide and/or a monosaccharide according to claim 1, wherein the organic material is a woody plant and/or a herbaceous plant.

7. The process for producing a polysaccharide and/or a monosaccharide according to claim 1, wherein the organic material is cellulose.

8. The process for producing a polysaccharide and/or a monosaccharide according to claim 1, wherein the organic material is a phenolic resin.

9. The process for producing a polysaccharide and/or a monosaccharide according to claim 1, wherein the polysaccharide to be hydrolyzed is a material having a β1-4 glycosidic bond.

10. The process for producing a polysaccharide and/or a monosaccharide according to claim 9, wherein the material having a β1-4 glycosidic bond is cellulose.

11. The process for producing a polysaccharide and/or a monosaccharide according to claim 9, wherein the material having a β1-4 glycosidic bond is a material comprising cellobiose.

12. The process for producing a polysaccharide and/or a monosaccharide according to claim 9, wherein the material having a β1-4 glycosidic bond is lignocellulose.

13. The process for producing a polysaccharide and/or a monosaccharide according to claim 1, wherein the monosaccharide is glucose.

14. A method for solubilizing cellulose or hemicellulose in water, which comprises reacting water with water-insoluble cellulose or water-insoluble hemicellulose in the presence of a carbonaceous material having sulfonic acid group therein,
    wherein the carbonaceous material having sulfonic acid group therein is produced by carbonizing an organic material at a temperature of 300 to 600° C. and subsequently sulfonating the resulting products with concentrated or fuming sulfuric acid at a temperature of 50 to 250° C., and
    wherein the hydrolysis of cellulose is greater than 3.1%.

* * * * *